United States Patent
Gojny et al.

(10) Patent No.: US 9,719,160 B1
(45) Date of Patent: Aug. 1, 2017

(54) STAINLESS STEEL ALLOYS WITH ANTIMICROBIAL PROPERTIES

(71) Applicants: Francis Joseph Gojny, Changshu Jiangsu (CN); Donald Jeen Chang Sun, San Gabriiel, CA (US)

(72) Inventors: Francis Joseph Gojny, Changshu Jiangsu (CN); Donald Jeen Chang Sun, San Gabriiel, CA (US)

( * ) Notice: Subject to any disclaimer, the term of this patent is extended or adjusted under 35 U.S.C. 154(b) by 0 days.

(21) Appl. No.: 15/075,193

(22) Filed: Mar. 20, 2016

(51) Int. Cl.
| | |
|---|---|
| *C22C 38/58* | (2006.01) |
| *C22C 38/44* | (2006.01) |
| *C22C 38/42* | (2006.01) |
| *C22C 38/04* | (2006.01) |
| *C22C 38/02* | (2006.01) |
| *C22C 38/00* | (2006.01) |
| *A01N 59/16* | (2006.01) |

(52) U.S. Cl.
CPC .............. *C22C 38/58* (2013.01); *A01N 59/16* (2013.01); *C22C 38/002* (2013.01); *C22C 38/005* (2013.01); *C22C 38/008* (2013.01); *C22C 38/02* (2013.01); *C22C 38/04* (2013.01); *C22C 38/42* (2013.01); *C22C 38/44* (2013.01)

(58) Field of Classification Search
CPC ... C22C 38/002; C22C 38/005; C22C 38/008; C22C 38/02; C22C 38/04; C22C 38/42; C22C 38/44; C22C 38/58; A01N 59/16
See application file for complete search history.

(56) References Cited

U.S. PATENT DOCUMENTS

2007/0062611 A1 * 3/2007 Murakami ........... C21D 8/1244
 148/111
2013/0092296 A1 * 4/2013 Qui ........................ C21D 1/18
 148/542

FOREIGN PATENT DOCUMENTS

CN 102994911 A * 3/2013 ............... C21D 8/02

OTHER PUBLICATIONS

Qiu, Dexin, English machine translation of CN 102994911A, Mar. 2013, p. 1-16.*

* cited by examiner

*Primary Examiner* — Roy King
*Assistant Examiner* — Caitlin Kiechle
(74) *Attorney, Agent, or Firm* — Patent Law & Venture Group; Gene Scott

(57) ABSTRACT

An austenitic antibacterial stainless steel formulation provides a high strength, highly corrosion resistant, antimicrobial product at a relatively low cost wherein antimicrobial performance is dramatic and greater mechanical properties and corrosion resistance are achieved as well. The alloy may comprise key constituents of Fe, Cr, Ni, and C plus a mischmetal having Ce and La components.

11 Claims, 2 Drawing Sheets

STAINLESS STEEL ALLOYS WITH ANTIMICROBIAL PROPERTIES

BACKGROUND

The field of this disclosure relates to antimicrobial metal alloy compositions and especially to stainless steel alloys with antimicrobial properties It is known that antimicrobial effects are shown by ions of mercury, silver, copper, iron, lead, zinc, bismuth, brass, gold, aluminum, and other metals. The technical paper; "Antibacterial Metals, a Viable Solution for Bacterial Attachment and Microbiologically Influenced Corrosion" by Kurissery et a provides an excellent overview of the importance of antimicrobial metals. Biofilm formation on surfaces is of concern to the public health. Also, biofilms are known to be deleterious to materials as they may induce corrosion. These reactions are referred to as biocorrosion or microbiologically influenced corrosion (MIC) when the underlying substratum is a metal or metal alloy. MIC is a serious problem in a number of industries including power generation, petrochemical, pulp and paper, gas transmission and shipbuilding. Conservative estimates place the direct cost of MIC at $30 to $50 billion per year at this time. The magnitude of the problem calls-for wider attention and collaboration between established research groups and laboratories that specialize in aspects of metal-microbe interactions. Such groups may focus on microbiology, metallurgy, civil & environmental engineering and biotechnology.

Stainless steel is widely used for architectural and decorative applications such as hand rails, faucets and other objects that receive continuous human contact. Stainless steel surfaces have no known antimicrobial effect. In the prior art we find that a small amount of copper is known to have been included as a constituent of stainless steel to achieve antimicrobial effects, but this approach is relatively expensive due to the cost of copper and the extra steps required in processing. Another problem is that such alloys exhibit lower corrosion resistance. Silver has also been used in stainless steel alloys but suffers the same issues as copper. Antimicrobial features in stainless steels have been shown to be effective against: Escherichia *coli, Candida Albicans*, HIV, and others microbes and viruses.

Antimicrobial coatings are known in the art as exemplified by U.S. Pat. No. 6,929,705 to Myers et al wherein a liquid dispersion containing metal component-supporting oxides and zeolite powders is applied to metal parts. Laminations such as taught in U.S. Pat. No. 7,521,489 to Shimazaki have been used wherein an antibacterial metal such as silver is used with layers of structural metals such as steel.

BRIEF SUMMARY AND OBJECTIVES

The presently disclosed stainless steel has alloying components that produce an antibacterial property, corrosion resistance and improved processability. Microscopic observations, quantitative bacteriostasis and selective mechanical tests show that a trace addition of an antibacterial alloying agent can homogeneously distribute in a 304 stainless steel matrix and can slightly improve its corrosion resistance. With an increase in the alloying addition, in some alloys clustering may occur, which reduces corrosion resistance and processability due to immiscible alloying constituents. Antibacterial additions in some stainless steel alloys exhibits the hormesis effect against *staphylococcus aureus* (*S. Aureus*) wherein a small addition may stimulate growth. In general, the greater the addition of the antibacterial agent, the better the antibacterial capability of the alloy.

DETAILED DESCRIPTION

An austenitic stainless steel alloy (the alloy) and its processing method is described. The alloy provides high strength, is highly corrosion resistant, and has strong antimicrobial properties while being able to be produced at a competitive cost. The alloy may comprise constituents of: iron, carbon, chrome, manganese, nickel, nitrogen, phosphorus, silicon, sulfur, molybdenum, copper, and tin in various amounts, and may include an antimicrobial compound (AC) which may be a mischmetal having Ce 70% and La 30% with these percentages being approximate ±10%, and may also include a grain refiner consisting of Cu 95% and Sn 5%, again approximately. In order to test the antimicrobial effectiveness of test specimens the alloy was produced and evaluated as described below.

Samples were produced using investment casting, and were solution treated at about 1050 degrees centigrade for about 30 minutes. Cast rods were sectioned and machined to produce disc specimens 25 mm in diameter and 2 mm in thickness. The specimens were polished and then cleaned using an ultrasonic bath.

For testing, the discs were sterilized by first autoclaving and then subjecting them to ultraviolet radiation. A thin film quantitative bacteriostasis method was used to evaluate antimicrobial performance according to the JIS z 2801-2000 (Japanese Industrial standard). A test strain of *staphylococcus* (s) *aureus* was introduced into a nutrient broth containing peptone and beef extract and then thoroughly homogenized mechanically to produce a microbial suspension. The suspension was diluted using a PbS buffer solution to produce a test material.

Figure 1:
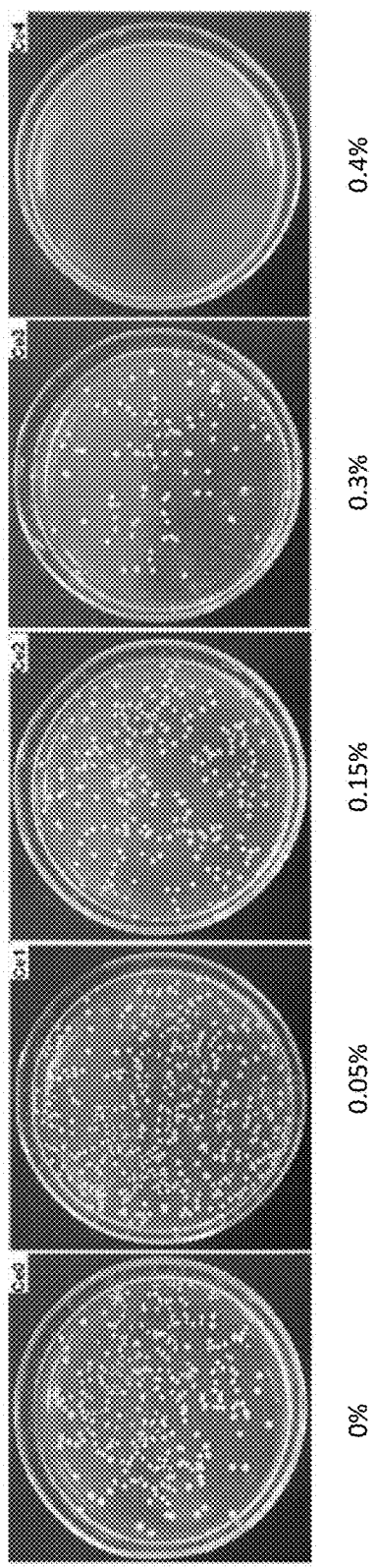
FIG. 1 illustrates samples showing antibacterial colonies indicating the effect of various levels of an antibacterial alloying component in 304 stainless steel.
Figure 2:
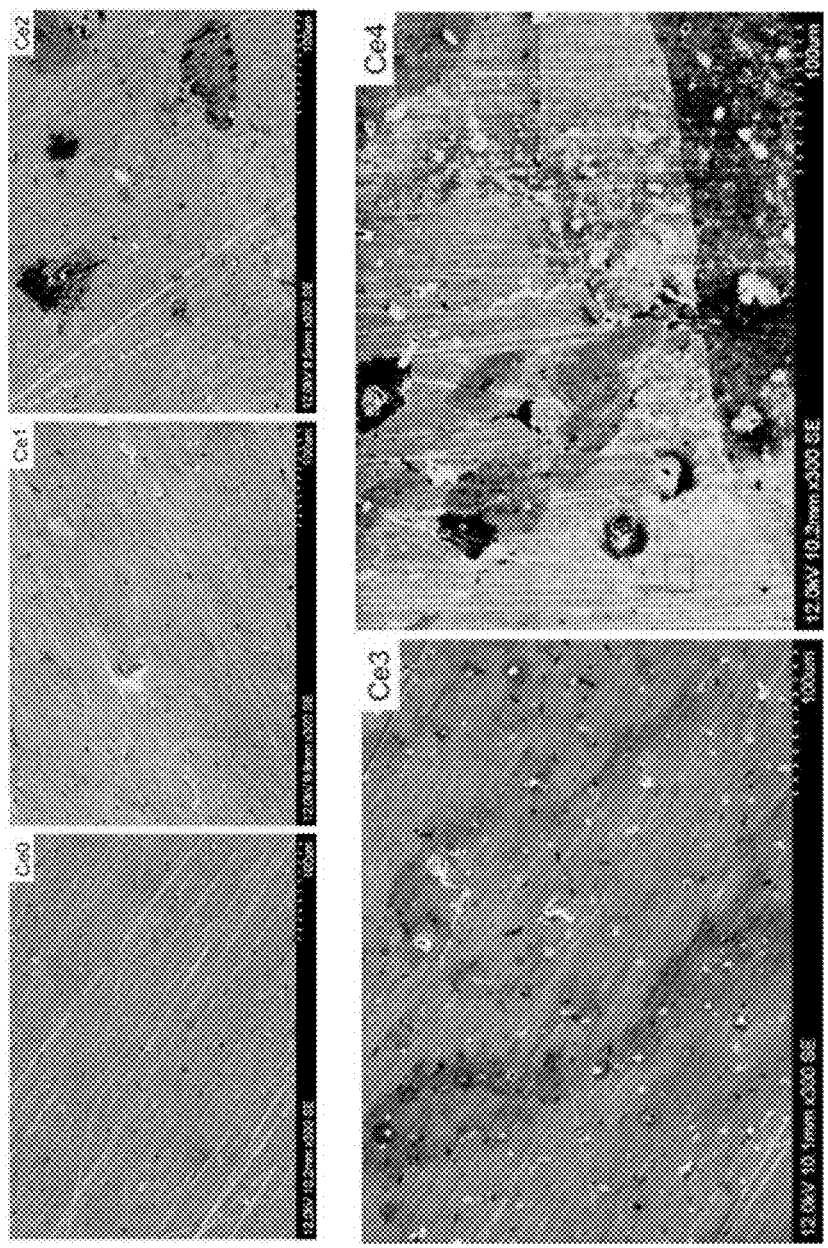
FIG. 2 illustrates topographies of the est specimens.

Fifty micro-liters of the test material was placed on each disc and then covered with a petri-slide allowing the test material to spread uniformly over the disc as a fluid thin film. Control samples were handled in the same manner substituting distilled water for the test material. All of the discs were held in an environmental chamber for 24 hours at 37° C. at over 90% relative humidity. Each specimen was then thoroughly washed with a highly dilute solution of the PbS buffer. An agar plate method was used to culture and perform a count of live microbes on each disc. All tests were carried out in triplicate. The relative sterilization rate of the microbes was calculated using:

$$R(\%) = (C-A)/C \times 100\%$$

Where R is the relative sterilization rate, C is the mean number of individual microbes counted on a control disc and A is the mean number of individual bacteria counted on a test disc. FIG. 1 shows the growth of s. *Aureus* on the discs. By counting the microbial colony numbers on each disc the effect of various percentages of the antimicrobial compound (AC) were estimated.

Results are shown below:

| AC % | R |
|---|---|
| 0 | — |
| 0.050 | −7.3 |
| 0.15 | 24.2 |
| 0.30 | 69.5 |
| 0.40 | 99.3 |

The following alloy partials were found to be effective in meeting the objectives, including alloying elements: Fe, Cr, Ni, Cu, and a mischmetal of at least 0.3 wt. %. Further, this alloy wherein the mischmetal includes about 70 wt. % Cu and 30 wt. % La. Further, this alloy with a grain refiner comprising Cu 95 wt. % and Sn 5 wt. %. Further, this alloy with at least one element selected from the group of elements consisting of carbon, manganese, nitrogen, phosphorus, silicon, sulfur, molybdenum, and tin. Further, wherein the Fe is at about 60 wt. %. Further, wherein the Cr is not more than 20 wt. %. Further, wherein the Ni is not more than 12 wt. %, and further wherein the Cu is not more than 2 wt. %.

In an alternate embodiment the antimicrobial stainless steel alloy may comprise by weight percent: up to 0.150 C, up to 20 Cr, up to 2.0 Mn, up to 12 Ni, up to 0.045 P, up to 1.0 Si, up to 0.030 S, 0.38 to 0.5 Ce, 1.48 to 3.1 Cu, 0.008 to 0.113 Sn and the balance Fe and impurities, and further comprising a mischmetal of at least 0.3 wt. %. The Ni may comprise not more than 10.5 weight percent, the Si may comprise not more than 0.75 weight percent, the N may comprise not more than 0.10 weight percent, the N may comprise between 0.10 and 0.16 weight percent and may alternately comprise between 0.16 and 0.30 weight percent. The C may comprise not more than 0.070 weight percent, while CR may comprise from 12.0 to 19.0 weight percent, and Ni may comprise not more than 14.0 weight percent, with Mo of not more than 3.0 weight percent.

Our conclusion is that the alloy does not exhibit any antimicrobial improvement when AC % is below 0.04; while instead, stimulated microbial growth is apparent. As the AC % increases however, the alloy gradually exhibits an antibacterial effectiveness. When the AC % is close to 0.38 sterilization efficiency is more than 99%, exhibiting an excellent antimicrobial effect. Our conclusion is also that we have discovered a means for producing stainless steel alloys that extinguish antimicrobial elements on their surfaces effectively without causing degradation to the fabricated article and without unreasonably increasing the cost of manufacture.

Embodiments of the subject apparatus and method have been described herein. Nevertheless, it will be understood that modifications may be made without departing from the spirit and understanding of this disclosure. Accordingly, other embodiments and approaches are within the scope of the following claims.

What is claimed is:

1. An antimicrobial stainless steel alloy comprising alloying elements: Fe, Cr, Ni, Cu, C, and between 0.10 to 0.30 wt. % N, and a mischmetal of at least 0.3 wt. %, wherein the C comprises not more than about 0.070 wt. % and further comprising a grain refiner comprising Cu 95 wt. % and Sn 5 wt. %.

2. The alloy of claim 1 further comprising at least one element selected from the group of elements consisting of manganese, phosphorus, silicon, sulfur, molybdenum, and tin.

3. The alloy of claim 1 wherein the Fe is at about 60 wt. %.

4. The alloy of claim 1 wherein the Cr is not more than 20 wt. %.

5. The alloy of claim 1 wherein the Ni is not more than 12 wt. %.

6. The alloy of claim 1 wherein the Cu is not more than 2 wt. %.

7. An antimicrobial stainless steel alloy comprising by weight percent:
up to 0.070 C, up to 20 Cr, up to 2.0 Mn, up to 14 Ni, up to 0.045 P, up to 1.0 Si, up to 0.030 S, 0.38 to 0.5 Ce, 1.48 to 3.1 Cu, 0.008 to 0.113 Sn, 0.10 to 0.30 N, and the balance Fe and impurities, and further comprising a mischmetal of at least 0.3 wt. %.

8. The alloy according to claim 7, wherein the Ni comprises not more than 10.5 weight percent.

9. The alloy according to claim 7, wherein the Si comprises not more than 0.75 weight percent.

10. The alloy according to claim 7, wherein the Cr comprises from 12.0 to 19.0 weight percent.

11. The alloy according to claim 7, further comprising Mo of not more than 3.0 weight percent.

* * * * *